United States Patent
Lee et al.

(10) Patent No.: US 10,429,737 B2
(45) Date of Patent: Oct. 1, 2019

(54) ANTIREFLECTIVE COMPOSITIONS WITH THERMAL ACID GENERATORS

(71) Applicant: Rohm and Haas Electronic Materials Korea Ltd., Cheonan, Chungcheongnam-Do (KR)

(72) Inventors: Jung-June Lee, Chungcheongnam-Do (KR); Jae Bong Lim, Chungcheongnam-Do (KR)

(73) Assignee: Rohm and Haas Electronic Materials Korea Ltd., Cheonan, Chungcheongnam-do (KR)

( * ) Notice: Subject to any disclaimer, the term of this patent is extended or adjusted under 35 U.S.C. 154(b) by 0 days.

(21) Appl. No.: 15/711,847

(22) Filed: Sep. 21, 2017

(65) Prior Publication Data

US 2019/0085173 A1 Mar. 21, 2019

(51) Int. Cl.

| | |
|---|---|
| *G03F 7/004* | (2006.01) |
| *G03F 7/26* | (2006.01) |
| *C09D 5/00* | (2006.01) |
| *G03F 7/09* | (2006.01) |
| *C07C 309/06* | (2006.01) |
| *C07D 277/22* | (2006.01) |
| *C07D 241/12* | (2006.01) |
| *C07D 263/32* | (2006.01) |
| *C07D 239/26* | (2006.01) |
| *H01L 21/027* | (2006.01) |
| *H01L 21/033* | (2006.01) |
| *G03F 7/11* | (2006.01) |
| *H01L 21/311* | (2006.01) |
| *C07D 213/75* | (2006.01) |
| *G03F 7/40* | (2006.01) |

(52) U.S. Cl.
CPC .............. *G03F 7/26* (2013.01); *C07C 309/06* (2013.01); *C07D 213/75* (2013.01); *C07D 239/26* (2013.01); *C07D 241/12* (2013.01); *C07D 263/32* (2013.01); *C07D 277/22* (2013.01); *C09D 5/006* (2013.01); *G03F 7/004* (2013.01); *G03F 7/091* (2013.01); *G03F 7/11* (2013.01); *G03F 7/40* (2013.01); *H01L 21/0274* (2013.01); *H01L 21/0276* (2013.01); *H01L 21/0332* (2013.01); *H01L 21/0337* (2013.01); *H01L 21/311* (2013.01)

(58) Field of Classification Search
CPC ... G03F 7/004; G03F 7/11; G03F 7/26; G03F 7/40; H01L 21/0274; H01L 21/0276; H01L 21/0332; H01L 21/0337; H01L 21/311; C07D 213/75
USPC ............ 430/271.1, 322, 325, 329, 300, 331
See application file for complete search history.

(56) References Cited

U.S. PATENT DOCUMENTS

| | | | |
|---|---|---|---|
| 6,767,689 B2 | 7/2004 | Pavelchek et al. | |
| 6,887,648 B2 | 5/2005 | Pavelchek et al. | |
| 8,623,589 B2 | 1/2014 | Kudo et al. | |
| 9,323,147 B2* | 4/2016 | Lee ......... | G03F 7/0233 |
| 9,405,188 B2* | 8/2016 | Lee ......... | G03F 7/0758 |
| 9,541,834 B2 | 1/2017 | Pohlers et al. | |
| 2010/0167203 A1* | 7/2010 | Cho ......... | C08G 77/50 430/272.1 |
| 2011/0117501 A1* | 5/2011 | Song ......... | C08G 61/02 430/315 |
| 2012/0270143 A1* | 10/2012 | Yun ......... | G03F 7/0752 430/14 |
| 2012/0270981 A1* | 10/2012 | Kim ......... | G03F 7/0752 524/317 |
| 2013/0037921 A1* | 2/2013 | Han ......... | C08L 83/06 257/635 |
| 2015/0118622 A1* | 4/2015 | Kang ......... | G03F 7/0226 430/286.1 |
| 2015/0212414 A1 | 7/2015 | Pohlers et al. | |
| 2017/0123313 A1* | 5/2017 | Kaur ......... | C07D 213/61 |
| 2017/0123314 A1* | 5/2017 | Kaur ......... | G03F 7/2022 |

* cited by examiner

*Primary Examiner* — Amanda C. Walke
(74) *Attorney, Agent, or Firm* — Mintz Levin Cohn Ferris Glovsky and Popeo, P.C.; Peter F. Corless

(57) ABSTRACT

New methods and substrates are provided that include antireflective compositions that comprise one or more thermal acid generators.

12 Claims, No Drawings

ANTIREFLECTIVE COMPOSITIONS WITH THERMAL ACID GENERATORS

FIELD

The present invention relates to new methods and substrates that include antireflective compositions that comprise one or more thermal acid generators.

INTRODUCTION

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating.

Known photoresists can provide features having resolution and dimension sufficient for many existing commercial applications. However for many other applications, the need exists for new photoresists and related materials and processes that can provide highly resolved images of submicron dimension.

Reflection of activating radiation used to expose a photoresist often poses limits on resolution of the image patterned in the photoresist layer. Reflection of radiation from the substrate/photoresist interface can produce spatial variations in the radiation intensity in the photoresist, resulting in non-uniform photoresist linewidth upon development. Radiation also can scatter from the substrate/photoresist interface into regions of the photoresist where exposure is non intended, again resulting in linewidth variations. The amount of scattering and reflection will typically vary from region to region, resulting in further linewidth non-uniformity. Variations in substrate topography also can give rise to resolution-limiting problems.

One approach used to reduce the problem of reflected radiation has been the use of a radiation absorbing layer interposed between the substrate surface and the photoresist coating layer. Such layers have also been referred to as antireflective layers or antireflective compositions. See U.S. Pat. No. 9,541,834; US20150212414; U.S. Pat. Nos. 6,767,689B2; 6,887,648B2; and 8,623,589.

It would be desirable to have new antireflective coating compositions for use with an overcoated photoresist composition.

SUMMARY

We have now discovered new methods that include use of antireflective compositions that comprise a resin component and one or more thermal acid generator compounds. Photoresists are applied over coating layers of the present antireflective compositions.

New antireflective coating compositions are also provided for use with an overcoated photoresist composition layer.

Particularly provided underlying antireflective compositions can exhibit enhanced coating properties. Preferred antireflective compositions also can harden or crosslink at relatively lower temperatures. See, for instance, the comparative results which follow.

We have found that use of a relatively hydrophilic polymer such as a polyester resin, or a resin comprising isocyanurate units, or a polyester resin containing isocyanurate substitution, can result in reduced defects upon lithographic processing of an overcoated photoresist layer. We also have found however that use of such a hydrophilic polymer can compromise coating coverage on the antireflective composition over an underlying substrate such as a microelectronic wafer, including as a result of undesired aggregation of the hydrophilic polymer as the antireflective composition layer is thermally treated to crosslink or otherwise harden the composition layer prior to applying the overcoating photoresist layer.

We have now found that the present antireflective compositions can undergo crosslinking or other hardening at relatively lower temperatures (e.g. 55° C., 60° C., 65° C. or 70° C. for 30 or 60 seconds). As such reduced hardening temperatures (onset temperatures), we have found improved coating layer quality of the hardened antireflective composition layer, including for antireflective compositions that comprise a hydrophilic resin component. Without being bound by any theory, that improved coating layer quality may result from reduced aggregation of the composition resin component during thermal treatment.

More specifically, in one preferred aspect, methods are provided that comprise:

a) applying on a substrate a layer of a coating composition comprising: 1) a resin; and 2) a thermal acid generator comprising a structure of Formula (I):

$$X \ominus \oplus YH \qquad (I)$$

wherein Y has a structure of Formula (II):

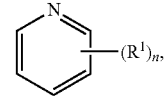

(II)

each $R^1$ is independently CN, $NO_2$, F, Cl, Br, I or $CF_3$; n is an integer of from 1 to 5; and X is an organic or inorganic anion component; and b) applying a layer of a photoresist composition above the coating composition layer.

A variety of anion X components may be employed including both organic and inorganic components, with organic components such as tosylate being often preferred. In certain aspects, preferred $R^1$ groups include CN, $NO_2$, Cl, Br, I and $CF_3$. In additional aspects, preferred $R^1$ groups may be CN, $NO_2$ and $CF_3$.

Preferred coating compositions of the invention also may comprise a separate crosslinker component. Such a crosslinker can react with the resin component such as during thermal treatment of a coating layer of the composition prior to applying a photoresist layer thereover.

A variety of resins may be used in the present underlying coating compositions. In certain embodiments, hydrophilic resins are preferred, such as a polyester resin, resins comprising cyanurate substitution including polyester resins that comprise cyanurate substitution. Preferably, in such compositions, one or more hydrophilic resins will comprise at least 50 weight percent of the total resin content of the coating composition, more preferably one or more hydrophilic resins will comprise at least 60, 70, 80, 90, 95 or even 100 weight percent of the total resin content of the coating composition.

In use with an overcoated photoresist, a coating composition may be applied on a substrate such as a semiconductor wafer which may have one or more organic or inorganic coating layers thereon. The applied coating layer may be optionally thermally treated prior to overcoating with a photoresist layer. As mentioned, such thermal treatment may cause hardening including crosslinking of the coating composition layer. Such crosslinking may include hardening and/or covalent-bonding forming reactions between one or more composition components and can modulate water contact angle of the coating composition layer.

Thereafter, a photoresist composition may be applied over the coating composition layer followed by imaging of the applied photoresist composition layer with patterned activating radiation and the imaged photoresist composition layer is developed to provide a photoresist relief image.

A variety of photoresists may be used in combination (i.e. overcoated) with a coating composition of the invention. Preferred photoresists for use with the underlying coating compositions of the invention are chemically-amplified resists that contain one or more photoactive compounds and a resin component that contains units that undergo a deblocking or cleavage reaction in the presence of photogenerated acid.

The invention further substrates (such as a microelectronic wafer substrate) coated with a coating composition of the invention alone or in combination with a photoresist composition.

Further provided are new antireflective coating compositions for use with an overcoated photoresist layer. Preferred antireflective compositions comprise 1) a resin; and 2) a thermal acid generator comprising a structure of Formula (IA):

$$X\ominus\oplus YH \qquad (IA)$$

wherein Y has a structure of Formula (IIA):

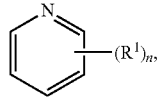

(IIA)

each $R^1$ is independently $C_1$-$C_6$ haloalkyl such as —$CF_3$, —CN, —$NO_2$, —$COR^2$, —$COOR^2$, —$CONR^2$ or —$SO_2R^2$; $R^2$ is independently hydrogen, $C_1$-$C_6$ alkyl, $C_3$-$C_6$ cycloalkyl or phenyl, which may be optionally substituted; n is an integer from 1 to 5; and X is an organic or inorganic anion component. Preferred $R^1$ groups of Formula IIA include —$CF_3$, —CN and —$NO_2$, acetyl, and ester. Preferred ester R1 groups will not be reactive (e.g. will not undergo or will significantly undergo bond-breaking reaction) during lithographic processing (e.g. during thermal treatment of imaging of an overcoated photoresist layer). Preferred X groups are organic components such as tosylate and the like.

Other aspects of the invention are disclosed infra.

DETAILED DESCRIPTION

In a preferred aspects, antireflective compositions for use with an overcoating photoresist composition are provided, where the antireflective composition comprises 1) a resin; and 2) a thermal acid generator comprising a structure of Formula (I):

$$X\ominus\oplus YH \qquad (IB)$$

wherein Y has a structure of Formula (IIB):

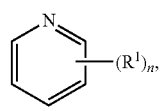

(IIB)

each $R^1$ is independently halogen, $C_1$-$C_6$ haloalkyl, —CN, —$NO_2$, —$COR^2$, —$COOR^2$, —$CONR^2$ or —$SO_2R^2$; $R^2$ is independently hydrogen, $C_1$-$C_6$ alkyl, $C_3$-$C_6$ cycloalkyl or phenyl, which may be optionally substituted; n is an integer from 0 to 5; and X is an organic or inorganic anion component.

In certain preferred aspects, $R^1$ is fluoroalkyl such as —$CF_3$. In preferred embodiments, as discussed above, each $R^1$ is independently CN, $NO_2$, F, Cl, Br, I or $CF_3$ or each $R^1$ is independently CN, $NO_2$, Cl, Br, I or $CF_3$. A variety of anion X components will be suitable with organic components such as tosylate often preferred.

In certain embodiments, the cation component of a thermal acid generator will not contain fluoro as a ring substituent. In certain embodiments, the cation component of a thermal acid generator will not contain any fluoro content. In certain embodiments, the cation component of a thermal acid generator will not contain any halogen content.

Preferred thermal acid generator compounds for use in the present antireflective composition may have a structure of the following Formula (A), (B) or (C):

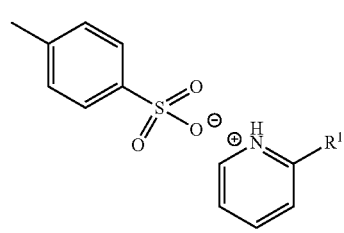

(A)

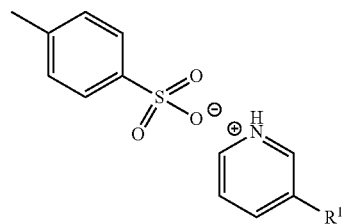

(B)

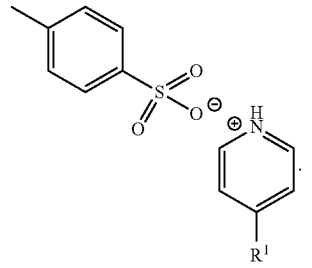

(C)

where in each of those Formulae (A), (B) or (C) $R^1$ is halogen, $C_1$-$C_6$ haloalkyl, —CN, —$NO_2$, —$COR^2$, —$COOR^2$, —$CONR^2$ or —$SO_2R^2$; and in certain preferred embodiments of Formulae (A), (B) or (C) $R^1$ is CN, $NO_2$, F, Cl, Br, I or CF$_3$, and in still further preferred embodiments of Formulae (A), (B) or (C) R$^1$ is CN, NO$_2$, Cl, Br, I or CF$_3$, or R$^1$ is CN, NO$_2$ or CF$_3$.

Specifically preferred thermal acid generators for use in the present antireflective compositions include the following. Also preferred are thermal acid generators that contain the below depicted substituted pyridyl cation component, but complexed to an anion component other than the shown tosylate:

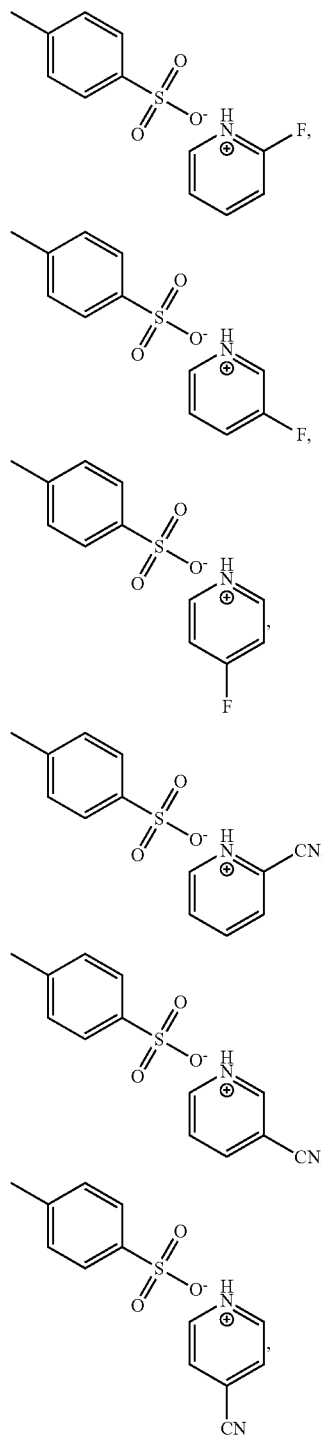

-continued

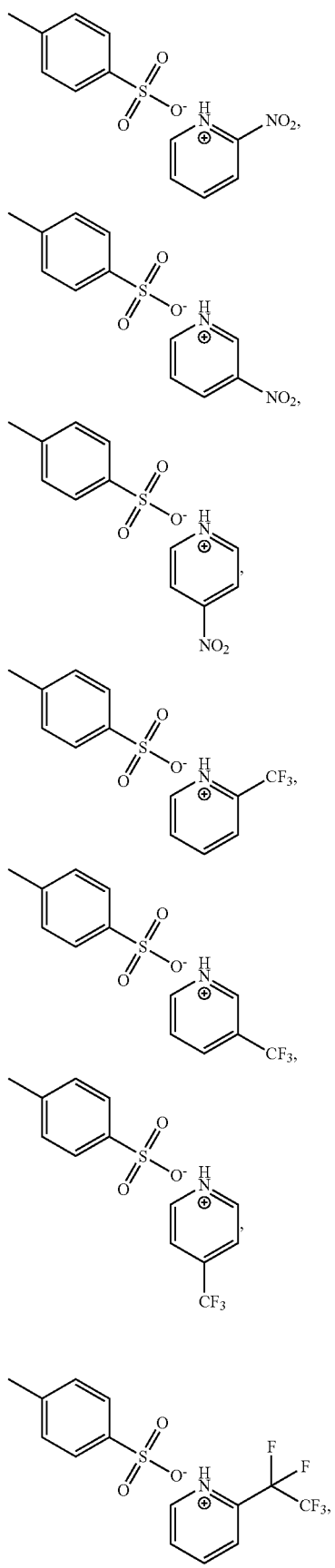

-continued
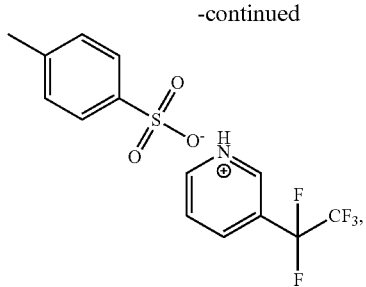
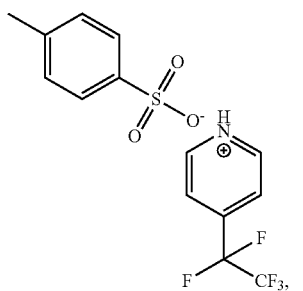
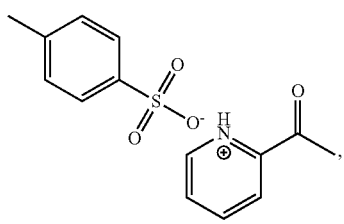
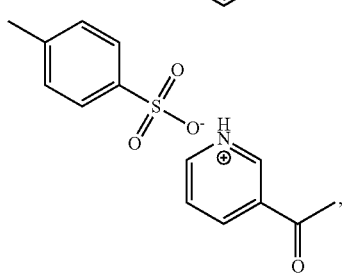
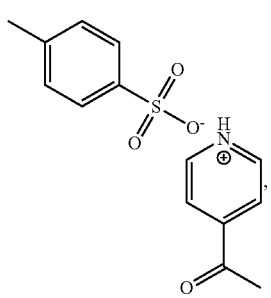
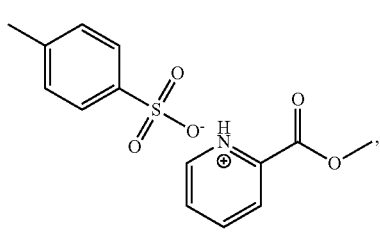
-continued
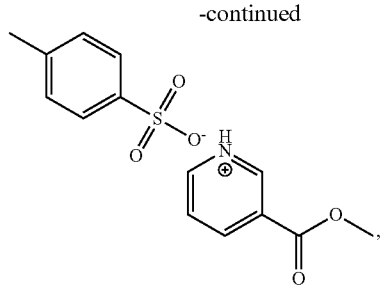
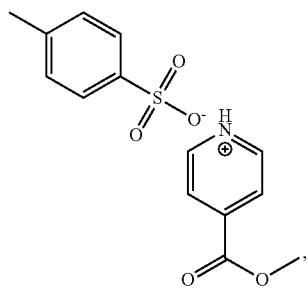
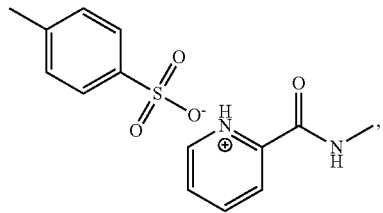
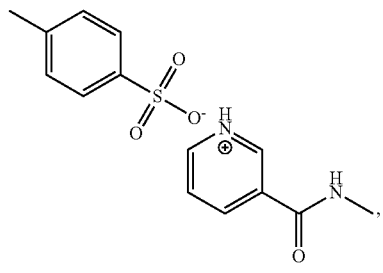
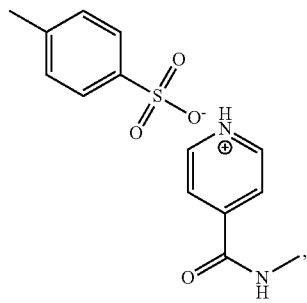
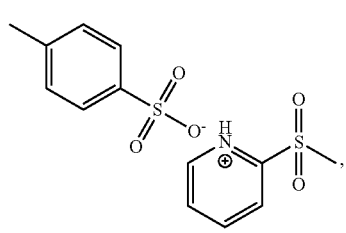

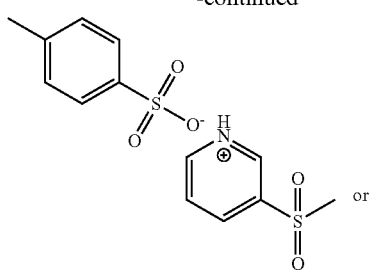
or
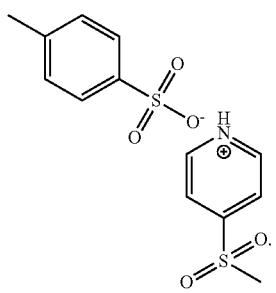
Particularly preferred thermal acid generators for use in the present antireflective compositions include the following. Also preferred are thermal acid generators that contain the below depicted substituted pyridyl cation component, but complexed to an anion component other than the shown tosylate.
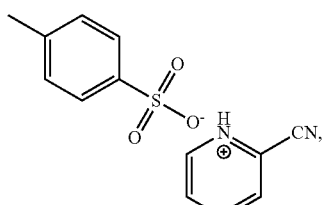
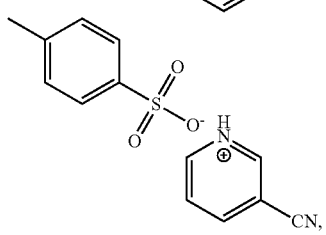
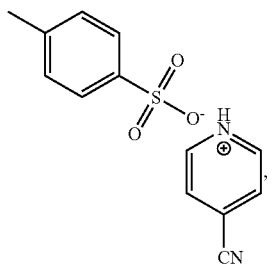
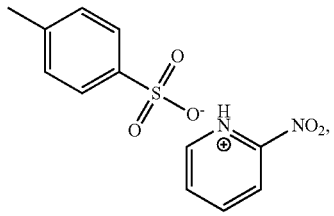
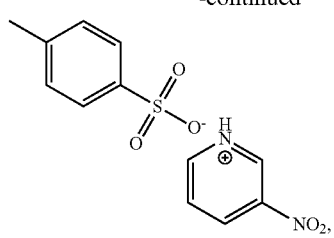
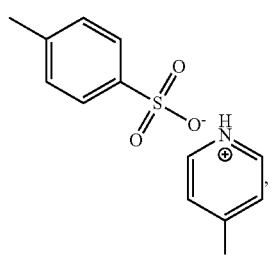
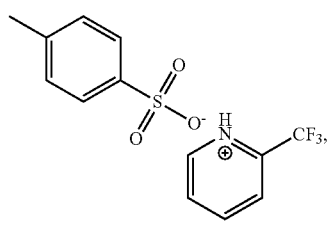
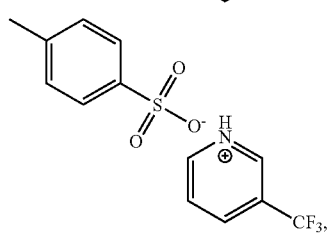
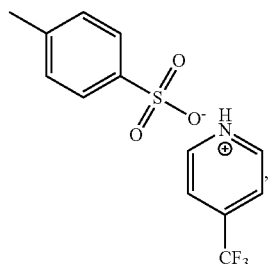
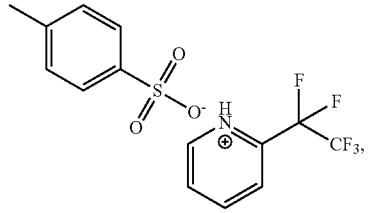
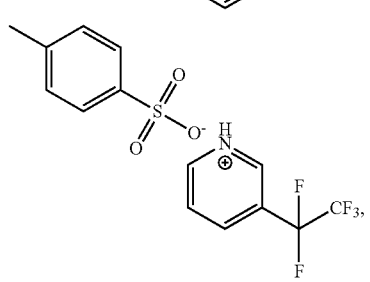

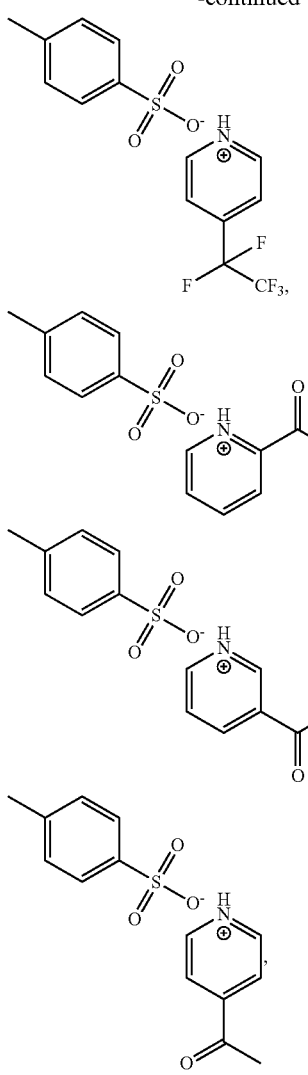
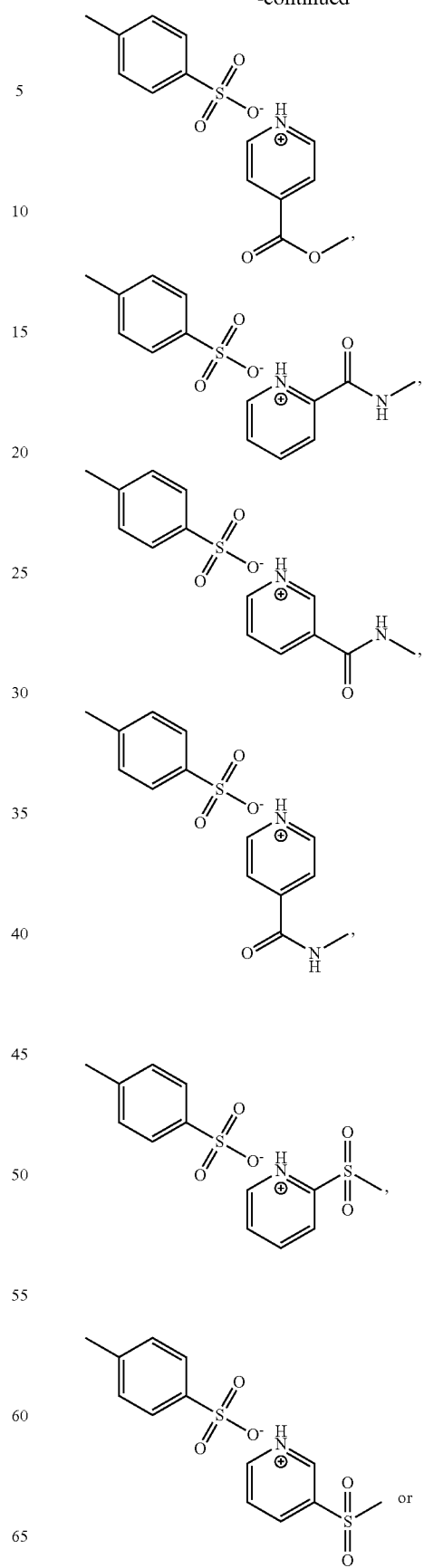

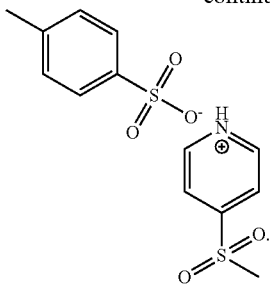

Advantageously, in certain embodiments, the thermal acid generator has an onset temperature (that is, a temperature at which acid is thermally generated) of not more than about 100° C., or not more than about 90° C., or not more than about 80° C., or not more than about 70° C., or not more than about 60° C.

As referred to herein, onset temperature of a thermal acid generator is determined by thermal treatment of a spin-coated composition film layer containing the thermal acid generator at a selected temperature for 60 seconds with thickness measurements made of both (i) the initial spin-coated composition film layer with thermal treatment at the selected temperature and (ii) the composition film layer after stripping by organic solvent (e.g. organic solvent of 50:50 v/v 2-hydroxyisobutyric acid methyl ester (HBM):propylene glycol methyl ether acetate (PGMEA). The onset temperature is the lowest temperature for crosslinking the film and the evaluated composition film layer containing the thermal acid generator is reduced in thickness by at least 10% after heat treatment compared to the final film thickness. See Example 9 for an exemplary protocol.

Preferred TAGs have relatively low molecular weight, for example, a molecular weight of less than or equal to 3000, more preferably ≤2500, ≤2000, ≤1500, ≤1000, ≤800 or even more preferably ≤500.

Typically one or more thermal acid generators are present in a coating composition in a concentration from about 0.1 to 10 percent by weight of the total of the dry components of the composition (all components except solvent carrier), more preferably about 0.5 to 2 percent by weight of the total dry components.

The present thermal acid generators can be readily prepared. For instance, a substituted pyridyl compound can be admixed with an anion component (e.g., for a tosyl anion component, 4-methylbenzenesulfonic acid hydrate can be admixed with a substituted pyridyl compound). See, for instance, Examples 2-4 which follow.

Particularly preferred resins of coating compositions of the invention may comprise polyester linkages. Polyester resins can be readily prepared by reaction of one or more polyol reagents with one or more carboxy-containing (such as a carboxylic acid, ester, anhydride, etc.) compounds. Suitable polyol reagents include diols, glycerols and triols such as e.g. diols such as diol is ethylene glycol, 1,2-propylene glycol, 1,3-propylene glycol, butane diol, pentane diol, cyclobutyl diol, cyclopentyl diol, cyclohexyl diol, dimethylolcyclohexane, and triols such as glycerol, trimethylolethane, trimethylolpropane and the like.

Preferably resins of underlying coating compositions of the invention will have a weight average molecular weight (Mw) of about 1,000 to about 10,000,000 daltons, more typically about 2,000 to about 10,000 daltons, and a number average molecular weight (Mn) of about 500 to about 1,000,000 daltons. Molecular weights (either Mw or Mn) of the resins of compositions of the invention are suitably determined by gel permeation chromatography.

The resin component will be the major solids component of an underlying coating composition in many preferred embodiments. For instance, one or resins suitably may be present from 50 to 99.9 weight percent based on total solid content of a coating composition, more typically from 80 or 85 to 95, 98 or 99+ (or even 100) weight percent based total solid content of a coating composition. As referred to herein, solids of a coating composition refer to all materials of the coating composition except solvent carrier.

Specifically preferred resins for use in the present underlying coating compositions include those that contain the following repeat units:

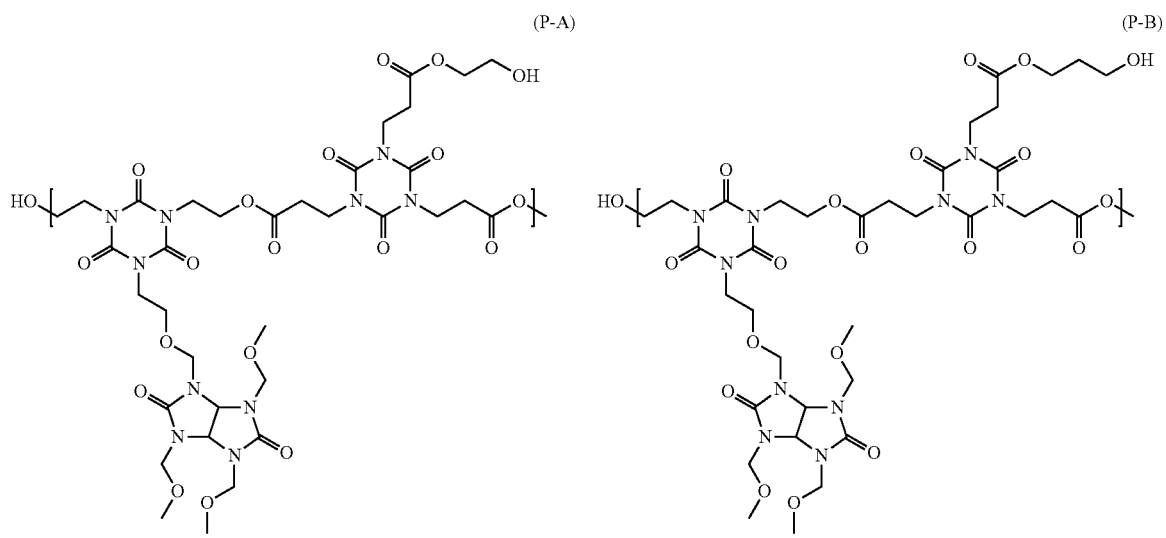

-continued
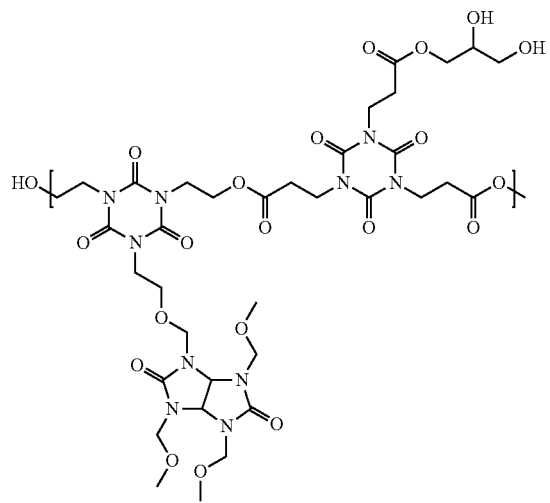
(P-C)
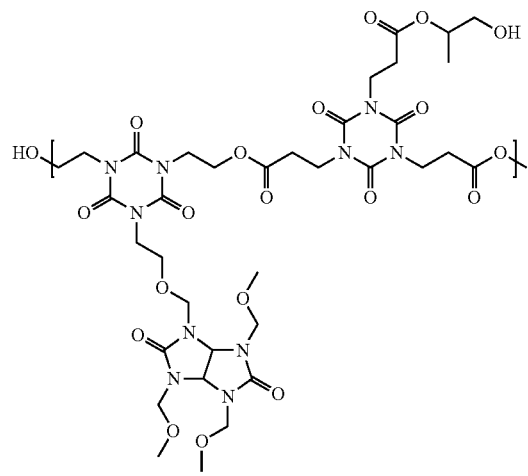
(P-D)
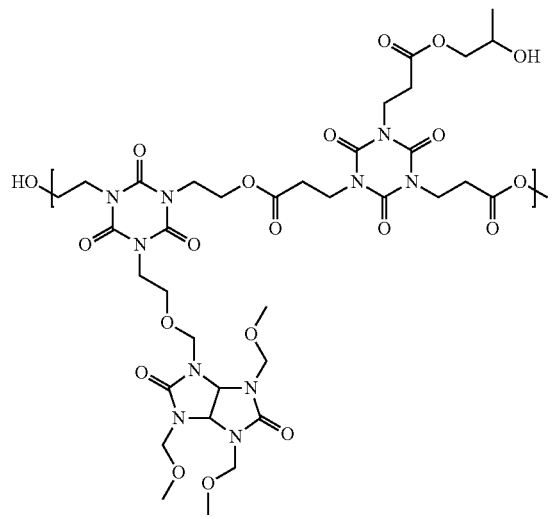
(P-E)

-continued
(P-F)
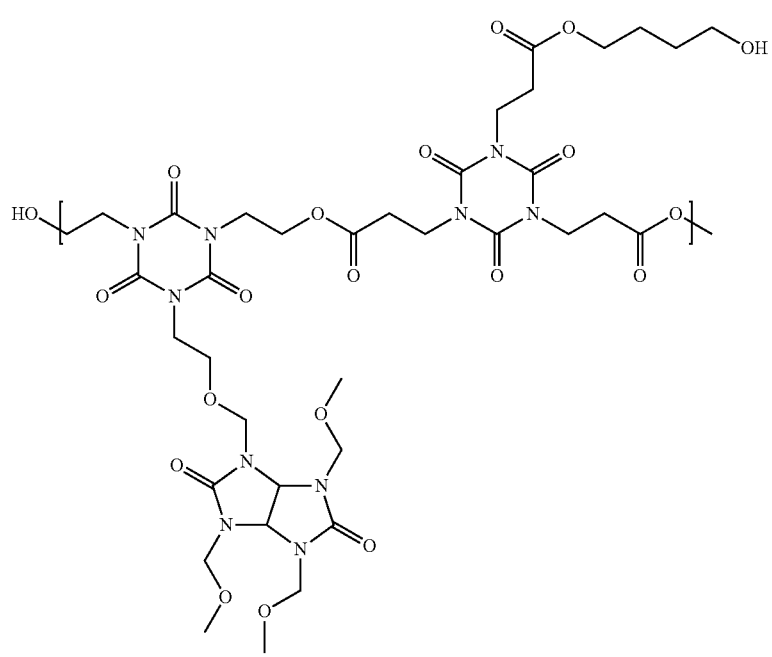
(P-G)
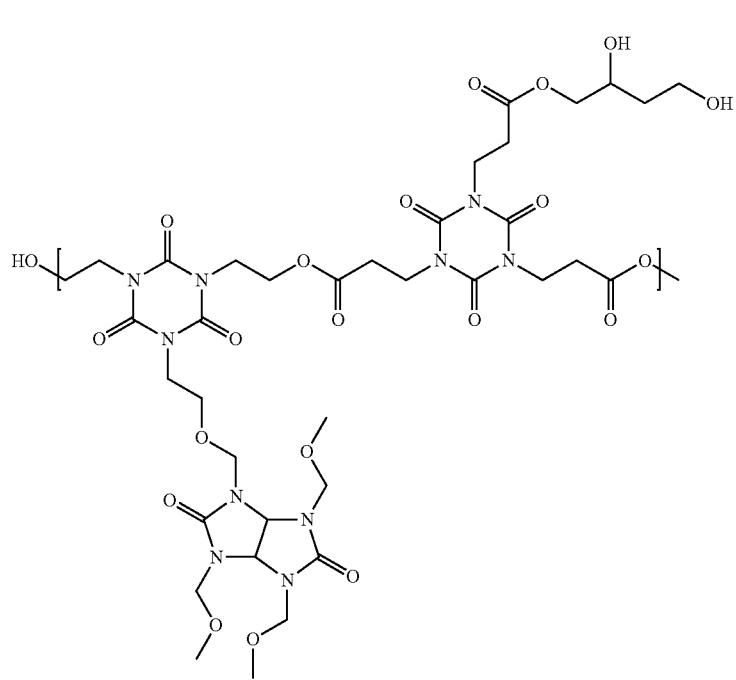

-continued
(P-H)
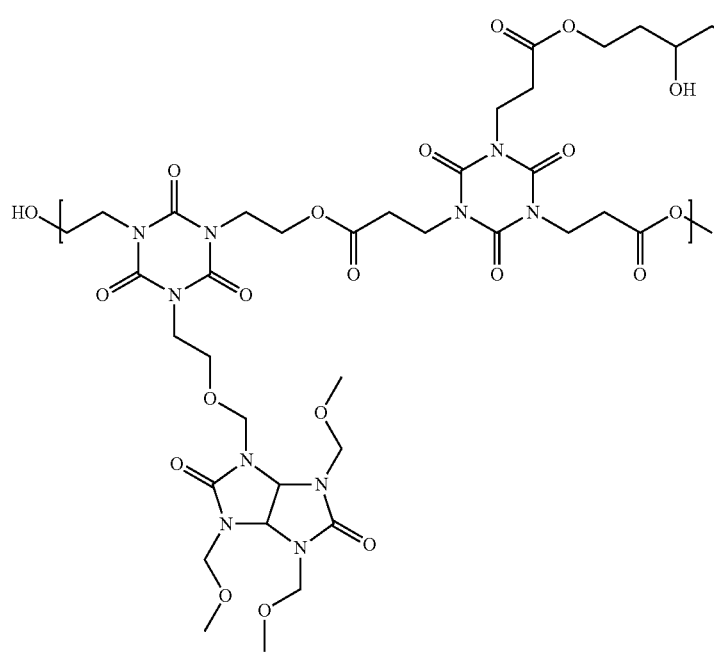
(P-I)
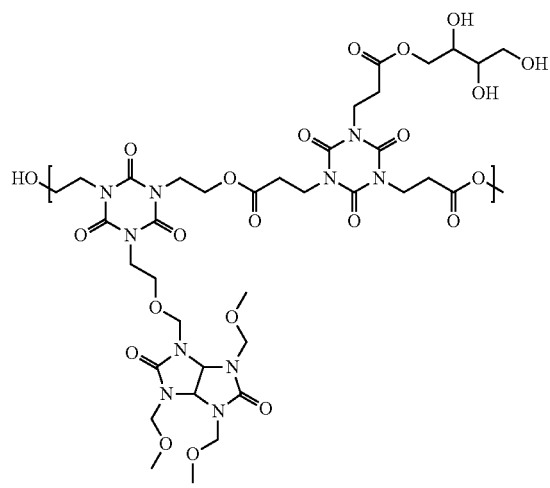
(P-J)
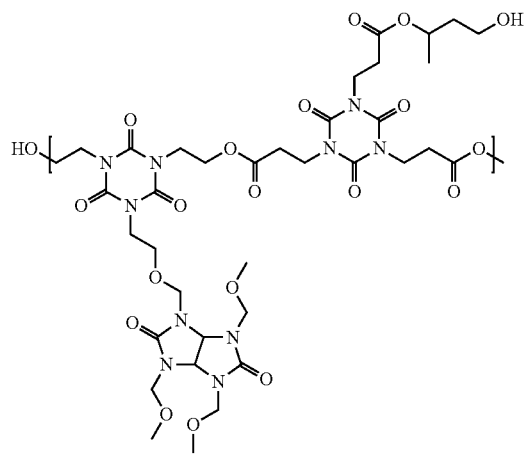
(P-K)
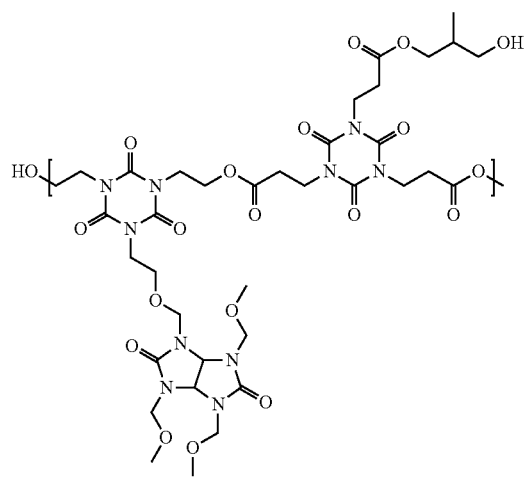
(P-L)
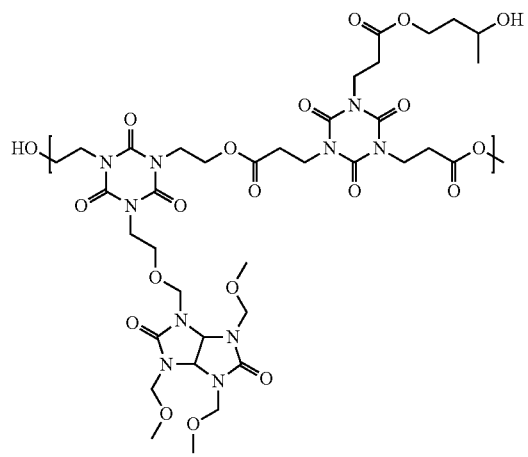

-continued
(P-M)
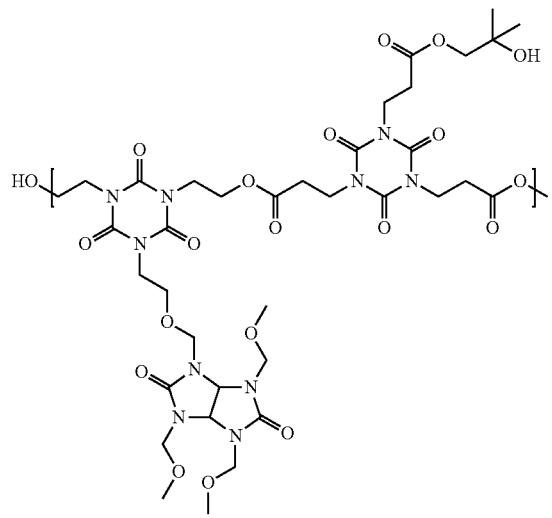
(P-N)
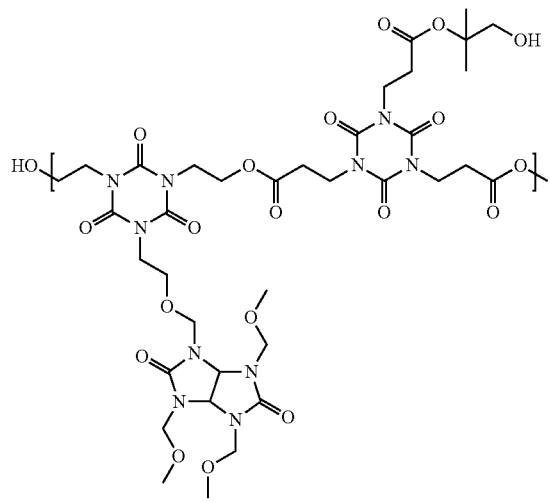
(P-O)
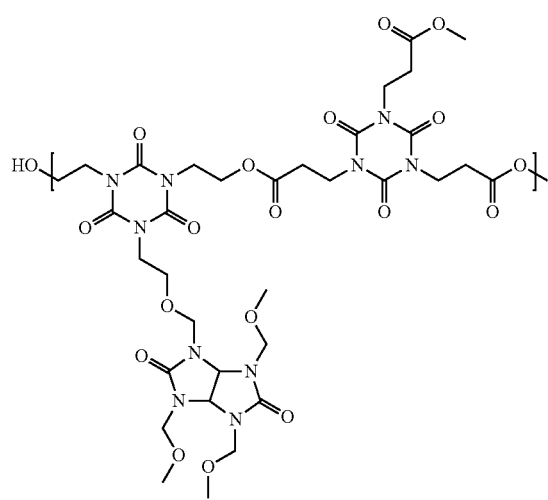
(P-P)
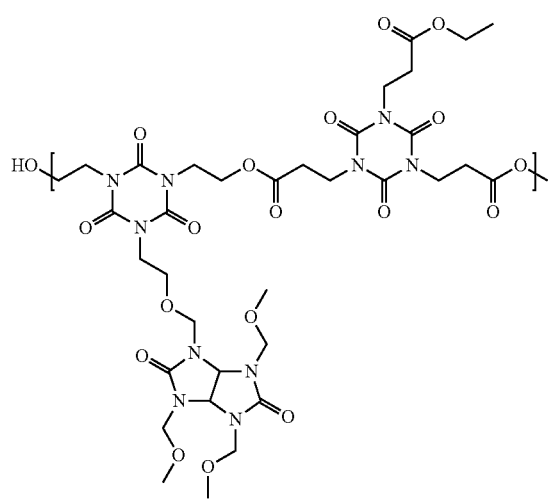
(P-Q)
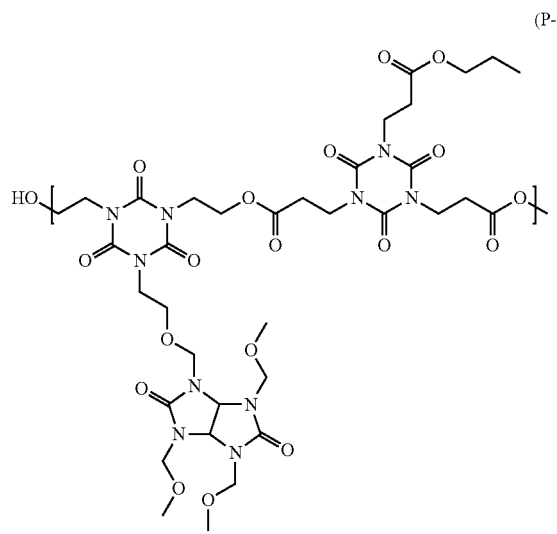
(P-R)
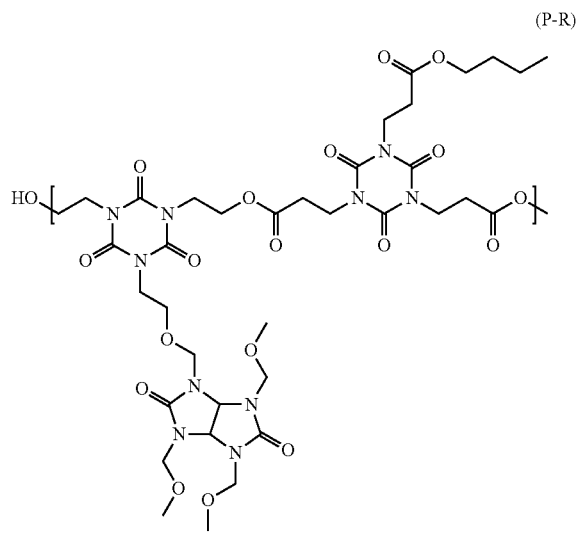

Suitable and preferred resins for use in the present underlying antireflective compositions can be readily prepared. See, for instance, Example 1, which follows and details reaction of an isocyanuarate reagent with a diol compound to provide a polyester cyanurate resin.

As discussed above, in certain embodiments, a coating composition of the invention may comprise a crosslinker in addition to or as a component of a resin. For example, coating compositions may include amine-based crosslinkers such as melamine materials, including melamine resins such as manufactured by Cytec Industries and sold under the tradename of Cymel 300, 301, 303, 350, 370, 380, 1116 and 1130; glycolurils including those glycolurils available from Cytec Industries; and benzoquanamines and urea-based materials including resins such as the benzoquanamine resins available from Cytec Industries under the name Cymel 1123 and 1125, and urea resins available from Cytec Industries under the names of Powderlink 1174 and 1196. In addition to being commercially available, such amine-based resins may be prepared e.g. by the reaction of acrylamide or methacrylamide copolymers with formaldehyde in an alcohol-containing solution, or alternatively by the copolymerization of N-alkoxymethyl acrylamide or methacrylamide with other suitable monomers.

Coating compositions of the invention, particularly for reflection control applications, also may contain additional dye compounds that absorb radiation used to expose an overcoated photoresist layer. Other optional additives include surface leveling agents, for example, the leveling agent available under the tradename Silwet 7604, or the surfactant FC 171 or FC 431 available from the 3M Company.

Underlying coating compositions of the invention also may contain other materials such as a photoacid generator, including a photoacid generator as discussed for use with an overcoated photoresist composition. See U.S. Pat. No. 6,261,743 for a discussion of such use of a photoacid generator in an antireflective composition.

To make a liquid underlying coating composition, the components of the coating composition are dissolved in a suitable solvent such as, for example, one or more oxyisobutyric acid esters particularly methyl-2-hydroxyisobutyrate, ethyl lactate or one or more of the glycol ethers such as 2-methoxyethyl ether (diglyme), ethylene glycol monomethyl ether, and propylene glycol monomethyl ether; solvents that have both ether and hydroxy moieties such as methoxy butanol, ethoxy butanol, methoxy propanol, and ethoxy propanol; methyl 2-hydroxyisobutyrate; esters such as methyl cellosolve acetate, ethyl cellosolve acetate, propylene glycol monomethyl ether acetate, dipropylene glycol monomethyl ether acetate and other solvents such as dibasic esters, propylene carbonate and gamma-butyro lactone. The concentration of the dry components in the solvent will depend on several factors such as the method of application. In general, the solid content of an underlying coating composition varies from about 0.5 to 20 weight percent of the total weight of the coating composition, preferably the solid content varies from about 0.5 to 10 weight of the coating composition.

Photoresists

Photoresists for use with an underlying coating composition typically comprise a polymer and one or more acid generators. Generally preferred are positive-tone resists and the resist polymer has functional groups that impart alkaline aqueous solubility to the resist composition. For example, preferred are polymers that comprise polar functional groups such as hydroxyl or carboxylate, or acid-labile groups that can liberate such polar moieties upon lithographic processing. Preferably the polymer is used in a resist composition in an amount sufficient to render the resist developable with an aqueous alkaline solution.

Acid generators are also suitably used with polymers that comprise repeat units containing aromatic groups, such as optionally substituted phenyl including phenol, optionally substituted naphthyl, and optionally substituted anthracene. Optionally substituted phenyl (including phenol) containing polymers are particularly suitable for many resist systems, including those imaged with EUV and e-beam radiation. For positive-acting resists, the polymer also preferably contains one or more repeat units that comprise acid-labile groups. For example, in the case of polymers containing optionally substituted phenyl or other aromatic groups, a polymer may comprise repeat units that contain one or more acid-labile moieties such as a polymer that is formed by polymerization of monomers of an acrylate or methacrylate compound with acid-labile ester (e.g. t-butyl acrylate or t-butyl methacrylate). Such monomers may be copolymerized with one or more other monomers that comprise aromatic group(s) such as optionally phenyl, e.g. a styrene or vinyl phenol monomer.

Preferred monomers used for the formation of such polymers include: an acid-labile monomer having the following formula (I), a lactone-containing monomer (II) and polarity control monomer of the following formula (III), or a combination comprising at least one of the foregoing monomers:

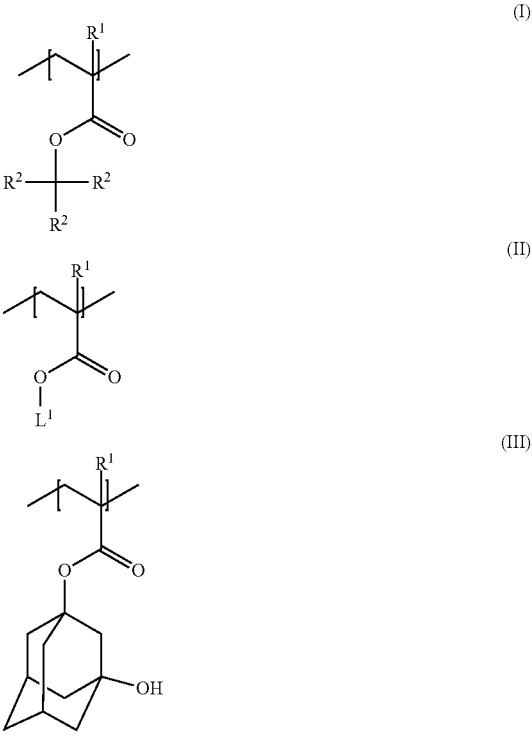

wherein each $R^1$ is independently H, F, —CN, $C_{1-6}$ alkyl, or $C_{1-6}$ fluoroalkyl. In the acid-deprotectable monomer of formula (I), $R^2$ is independently $C_{1-20}$ alkyl, $C_{3-20}$ cycloalkyl, or $C_{6-20}$ aryl, and each $R^2$ is separate or at least one $R^2$ is bonded to an adjacent $R^2$ to form a cyclic structure. In lactone-containing monomer of formula (II), $L^1$ is a monocyclic, polycyclic, or fused polycyclic $C_{4-20}$ lactone-containing group.

The unit of general formula (I) includes an acid labile group that undergoes a photoacid-promoted deprotection reaction on exposure to activating radiation and heat treatment. This allows for a switch in polarity of the matrix polymer, leading to a change in solubility of the polymer and photoresist composition in an organic developer. Suitable monomers for forming units of formula (I) include, for example, the following:

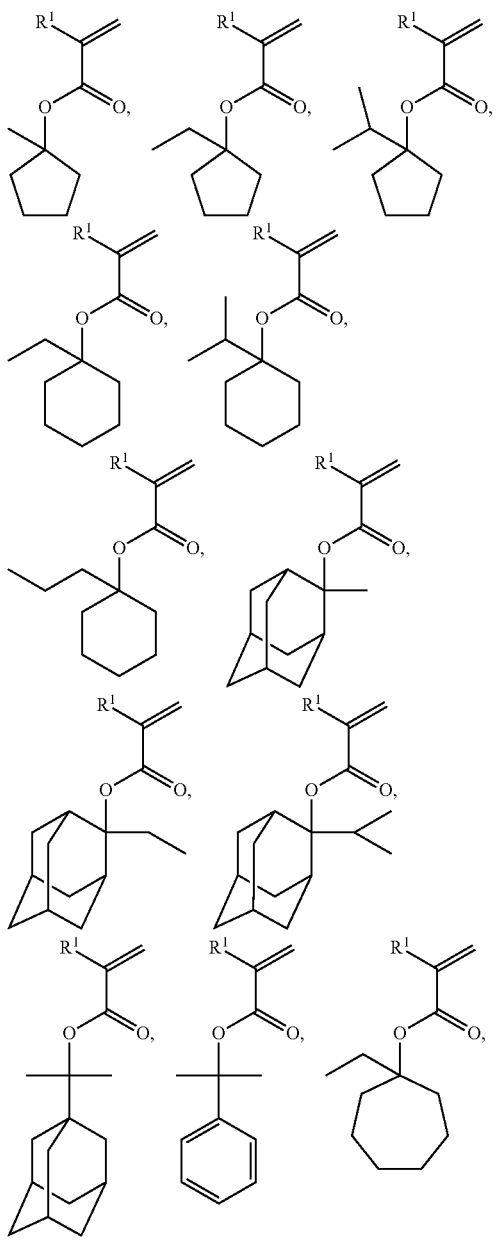

or a combination comprising at least one of the foregoing monomers, wherein $R^1$ is H, F, —CN, $C_{1-6}$ alkyl, or $C_{1-6}$ fluoroalkyl.

The unit of general formula (II) includes a lactone moiety effective to control the dissolution rate of the matrix polymer and photoresist composition. Suitable monomers for forming units of general formula (II) include, for example, the following:

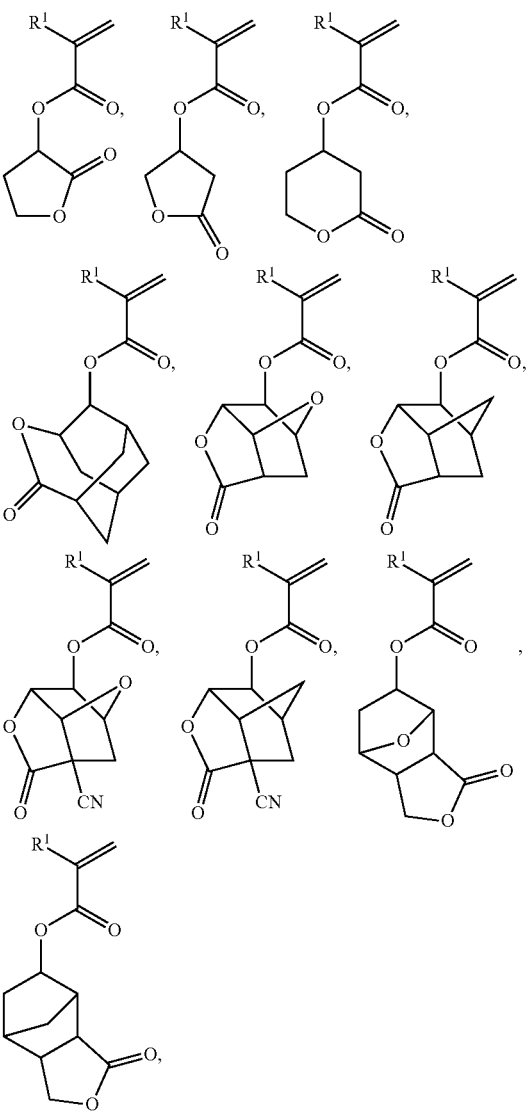

or a combination comprising at least one of the foregoing monomers, wherein $R^1$ is H, F, —CN, $C_{1-6}$ alkyl, or $C_{1-6}$ fluoroalkyl.

The unit of formula (III) provides a polar group, which enhances etch resistance of the resin and photoresist composition and provides additional means to control the dissolution rate of the resin and photoresist composition. Monomers for forming the unit of formula (III) include 3-hydroxy-1-adamantyl methacrylate (HAMA) and preferably 3-hydroxy-1-adamantyl acrylate (HADA).

The resin can include one or more additional units of general formulae (I), (II) and/or (III) different from the first units. Where additional such units are present in the resin, they will preferably include an additional leaving group-containing unit of formula (I) and/or a lactone-containing unit of formula (II).

In addition to the polymerized units described above, the resin can include one or more additional units which are not of general formula (I), (II) or (III). For example, a particularly suitable lactone group-containing unit is of the following general formula (IV):

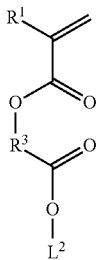

(IV)

wherein: $R^1$ is H, F, —CN, $C_{1-6}$ alkyl, or $C_{1-6}$ fluoroalkyl, heterocycloalkyl, $R^3$ is a $(C_1-C_3)$alkylene group and $L^2$ is a lactone group. The following exemplary monomers are suitable for use in forming the additional lactone unit of general formula (IV):

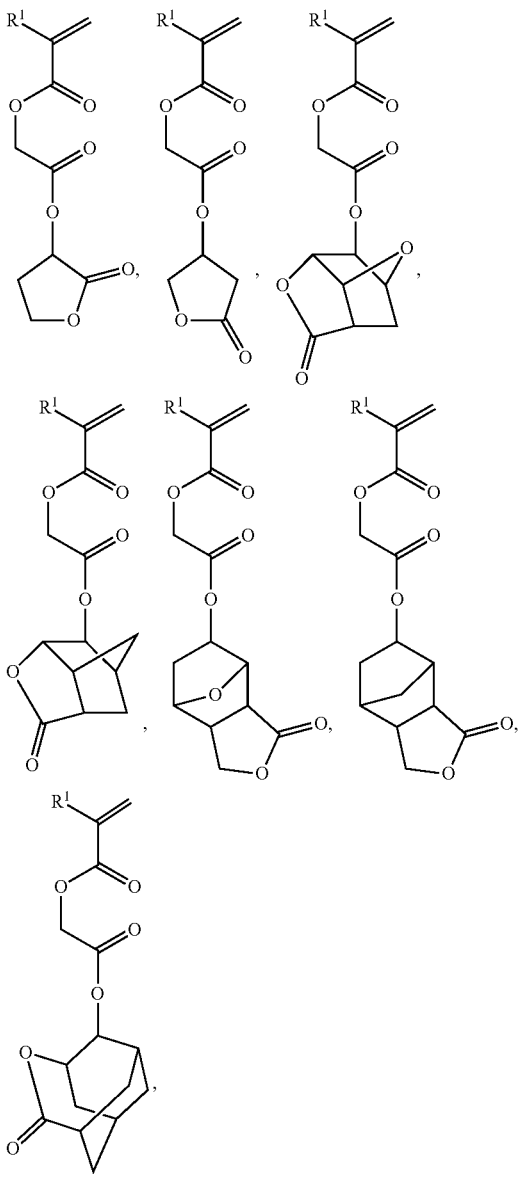

or a combination comprising at least one of the foregoing monomers, wherein $R^1$ is H, F, —CN, $C_{1-6}$ alkyl, or $C_{1-6}$ fluoroalkyl.

Specifically suitable polymers that have acid-labile deblocking groups for use in a positive-acting chemically-amplified photoresist of the invention have been disclosed in European Patent Application 0829766A2 (polymers with acetal and ketal polymers) and European Patent Application EP0783136A2 (terpolymers and other copolymers including units of 1) styrene; 2) hydroxystyrene; and 3) acid labile groups, particularly alkyl acrylate acid labile groups.

Polymers for use in photoresists of the invention may suitably vary widely in molecular weight and polydisperity. Suitable polymers include those that have an $M_w$ of from about 1,000 to about 50,000, more typically about 2,000 to about 30,000 with a molecular weight distribution of about 3 or less, more typically a molecular weight distribution of about 2 or less.

Preferred negative-acting compositions of the invention comprise a mixture of materials that will cure, crosslink or harden upon exposure to acid, and two or more acid generators as disclosed herein. Preferred negative acting compositions comprise a polymer binder such as a phenolic or non-aromatic polymer, a crosslinker component and a photoactive component of the invention. Such compositions and the use thereof have been disclosed in European Patent Applications 0164248 and U.S. Pat. No. 5,128,232 to Thackeray et al. Preferred phenolic polymers for use as the polymer binder component include novolaks and poly(vinylphenol)s such as those discussed above. Preferred crosslinkers include amine-based materials, including melamine, glycolurils, benzoguanamine-based materials and urea-based materials. Melamine-formaldehyde polymers are often particularly suitable. Such crosslinkers are commercially available, e.g. the melamine polymers, glycoluril polymers, urea-based polymer and benzoguanamine polymers, such as those sold by Cytec under tradenames Cymel 301, 303, 1170, 1171, 1172, 1123 and 1125 and Beetle 60, 65 and 80.

Particularly preferred photoresists of the invention may be used in immersion lithography applications. See, for example, U.S. Pat. No. 7,968,268 to Rohm and Haas Electronic Materials for a discussion of preferred immersion lithography photoresists and methods.

Photoresists of the invention also may comprise a single acid generator or a mixture of distinct acid generators, typically a mixture of 2 or 3 different acid generators, more typically a mixture that consists of a total of 2 distinct acid generators. The photoresist composition comprises an acid generator employed in an amount sufficient to generate a latent image in a coating layer of the composition upon exposure to activating radiation. For example, the acid generator will suitably be present in an amount of from 1 to 20 wt % based on total solids of the photoresist composition.

Suitable acid generators are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine.

As referred to herein, acid generators can produce an acid when exposed to activating radiation, such as EUV radiation, e-beam radiation, 193 nm wavelength radiation or other radiation sources. Acid generator compounds as referred to herein also may be referred to as photoacid generator compounds.

Photoresists of the invention also may contain other materials. For example, other optional additives include actinic and contrast dyes, anti-striation agents, plasticizers, speed enhancers and sensitizers. Such optional additives typically will be present in minor concentration in a photoresist composition.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as tripropylamine, dodecylamine, tris(2-hydroxypropyl)amine, oltetrakis(2-hydroxypropyl)ethylenediamine; aryl amines such as diphenylamine, triphenylamine, aminophenol, and 2-(4-aminophenyl)-2-(4-hydroxyphenyl)propane, a hindered amine such as diazabicycloundecene (DBU) or diazabicyclononene (DBN), or ionic quenchers including quaternary alkyl ammonium salts such as tetrabutylammonium hydroxide (TBAH) or tetrabutylammonium lactate. Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

Lithographic Processing

In use, a coating composition of the invention is applied as a coating layer to a substrate by any of a variety of methods such as spin coating. The coating composition in general is applied on a substrate with a dried layer thickness of between about 0.02 and 0.5 µm, preferably a dried layer thickness of between about 0.04 and 0.20 µm. The substrate is suitably any substrate used in processes involving photoresists. For example, the substrate can be silicon, silicon dioxide or aluminum-aluminum oxide microelectronic wafers. Gallium arsenide, silicon carbide, ceramic, quartz or copper substrates may also be employed. Substrates for liquid crystal display or other flat panel display applications are also suitably employed, for example glass substrates, indium tin oxide coated substrates and the like. Substrates for optical and optical-electronic devices (e.g. waveguides) also can be employed.

Preferably the applied coating layer is cured before a photoresist composition is applied over the underlying coating composition. Cure conditions will vary with the components of the underlying coating composition. Particularly the cure temperature will depend on the specific acid or acid (thermal) generator that is employed in the coating composition. Typical cure conditions are from about 60° C. to 225° C. for about 0.5 to 5 minutes. We have found that coating layer of preferred antireflective compositions as disclosed herein may effectively undergo hardening at relatively lower temperatures such as 55° C. or 60° C.-75° C. Cure conditions preferably render the coating composition coating layer substantially insoluble to the photoresist solvent as well the developer solution to be used.

After such curing, a photoresist is applied above the surface of the applied coating composition. As with application of the bottom coating composition layer(s), the overcoated photoresist can be applied by any standard means such as by spinning, dipping, meniscus or roller coating. Following application, the photoresist coating layer is typically dried by heating to remove solvent preferably until the resist layer is tack free. Optimally, essentially no intermixing of the bottom composition layer and overcoated photoresist layer should occur.

The resist layer is then imaged with activating radiation such as 248 nm, 193 nm or EUV radiation through a mask in a conventional manner. The exposure energy is sufficient to effectively activate the photoactive component of the resist system to produce a patterned image in the resist coating layer. Typically, the exposure energy ranges from about 3 to 300 mJ/cm$^2$ and depending in part upon the exposure tool and the particular resist and resist processing that is employed. The exposed resist layer may be subjected to a post-exposure bake if desired to create or enhance solubility differences between exposed and unexposed regions of a coating layer. For example, negative acid-hardening photoresists typically require post-exposure heating to induce the acid-promoted crosslinking reaction, and many chemically amplified positive-acting resists require post-exposure heating to induce an acid-promoted deprotection reaction. Typically post-exposure bake conditions include temperatures of about 50° C. or greater, more specifically a temperature in the range of from about 50° C. to about 160° C.

The photoresist layer also may be exposed in an immersion lithography system, i.e. where the space between the exposure tool (particularly the projection lens) and the photoresist coated substrate is occupied by an immersion fluid, such as water or water mixed with one or more additives such as cesium sulfate which can provide a fluid of enhanced refractive index. Preferably the immersion fluid (e.g., water) has been treated to avoid bubbles, e.g. water can be degassed to avoid nanobubbles.

References herein to "immersion exposing" or other similar term indicates that exposure is conducted with such a fluid layer (e.g. water or water with additives) interposed between an exposure tool and the coated photoresist composition layer.

The exposed photoresist layer is then treated with a suitable developer capable of selectively removing portions of the film to form a photoresist pattern. In a negative tone development (NTD) process, unexposed regions of a photoresist layer can be selectively removed by treatment with a suitable nonpolar solvent. See U.S. 2011/0294069 for suitable procedures for negative tone development. Typical nonpolar solvents for negative tone development are organic developers, such as a solvent chosen from ketones, esters, hydrocarbons, and mixtures thereof, e.g. acetone, 2-hexanone, 2-heptanone, methyl acetate, butyl acetate, and tetrahydrofuran. Photoresist materials used in the NTD process preferably form a photoresist layer that can form a negative image with organic solvent developer or a positive image with aqueous base developer such as tetraalkylammonium hydroxide solution. Preferably, the NTD photoresist is based on a polymer having acid sensitive (deprotectable) groups which, when deprotected, form carboxylic acid groups and/or hydroxyl groups.

Alternatively, development of the exposed photoresist layer can be accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups which form carboxylic acid groups when deprotected, and the developer is preferably a metal-ion free tetraalkylammonium hydroxide solution, such as, for example, aqueous 0.26 N tetramethylammonium hydroxide. A pattern forms by developing.

The developed substrate may then be selectively processed on those substrate areas bared of photoresist, for example, chemically etching or plating substrate areas bared of photoresist in accordance with procedures well known in the art. Suitable etchants include a hydrofluoric acid etching solution and a plasma gas etch such as an oxygen plasma etch. A plasma gas etch removes the underlying coating layer.

As discussed, in certain aspects, a wet etch process may be suitably employed. Wet etching may be suitably carried out by exposing the surface to be etched (e.g. a metal nitride, or metal nitride coated with one or more organic and/or inorganic layers) with a wet etch composition for a time and temperature effective to etch the surface (e.g. metal nitride surface and/or coating layers thereon). Exemplary wet etching compositions include an aqueous mixture of ammonium hydroxide and a peroxide such as hydrogen peroxide, or a mixture of an acid such as sulfuric acid and a peroxide such as hydrogen peroxide. See US 2006/0226122 for exemplary compositions. The examples which follow also provide exemplary wet etch process conditions. As referred to herein, a "wet etch process" means treating substrate areas defined by a adjoining photoresist (after development of the photoresist image) with a fluid composition typically either acid or alkaline in combination with a peroxide agent, but in any event distinguished from a plasma dry etch.

The following non-limiting examples are illustrative of the invention.

Example 1: Polymer Synthesis

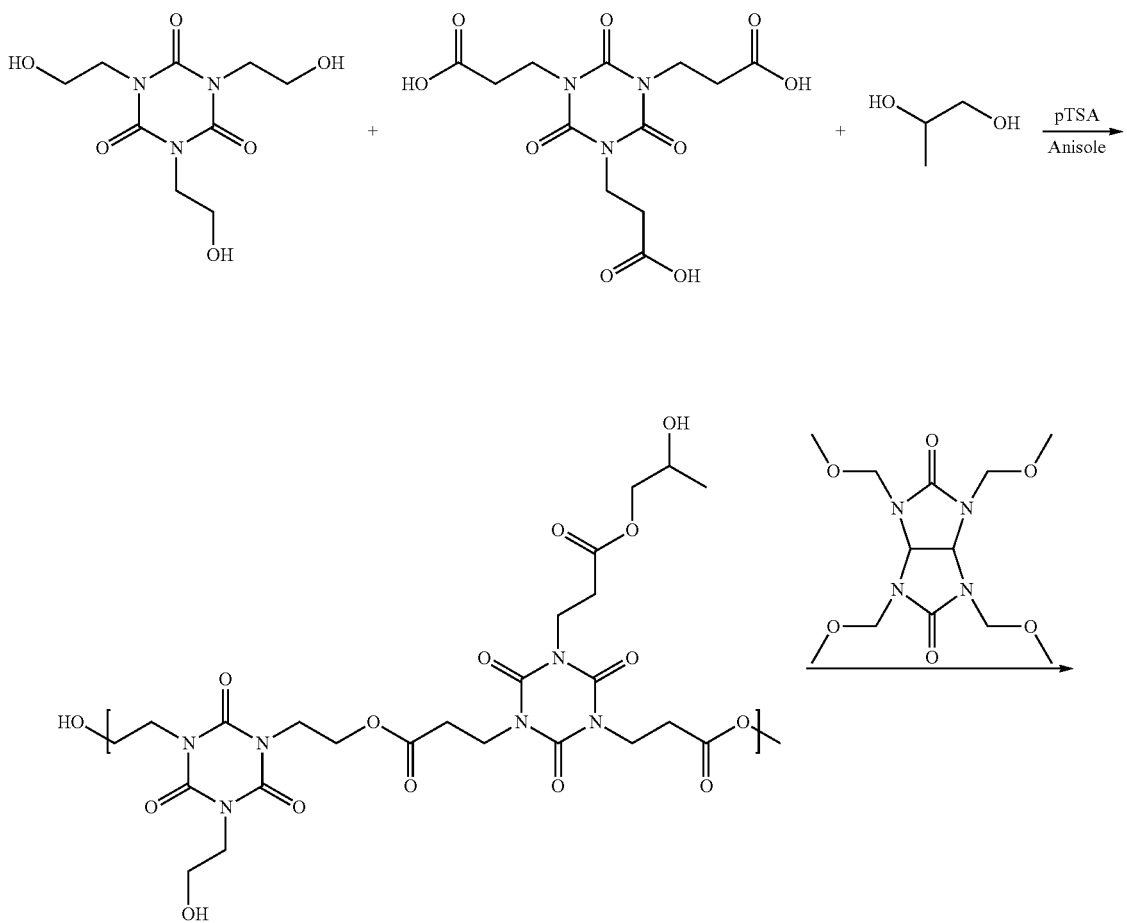

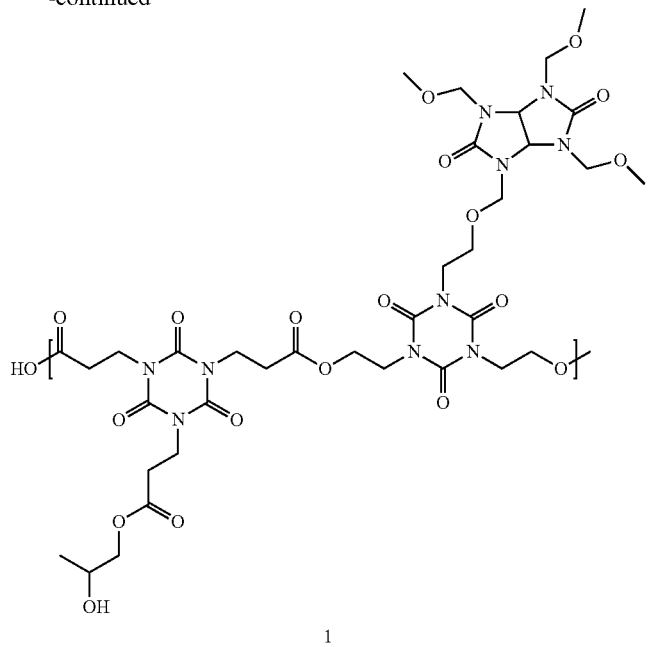

1

A resin having repeat units of structure 1 was prepared as depicted in the above Scheme and as follows. A 3-necked 250 ml round bottom flask was equipped with a thermocouple, Dean-stark, condenser and a heating oil bath. Tris (2-hydroxyethyl)isocyanurate (34.44 g, 131.8 mmol), Tris (2-carboxyethyl)isocyanurate (45.50 g, 131.8 mmol), 1,2-Propandiol (20.06 g, 263.7 mmol), p-Toulenesulfonic acid (p-TSA) (1.00 g, 5.3 mmol) and 34 g of anisole were weighed into a flask. It was heated up to a set temperature (150° C.) with stirring for 40 min. The solution was then cooled to the room temperature. The cooled solution was quenched with triethylamine (0.53 g, 5.3 mmol) and diluted with HBM (80 g) for the isolation. Reaction mixture was precipitated with methyl tert-butyl ether (MTBE) (800 g) and then filtered and vacuum dried for 24 hrs at 40° C. A 3-necked 100 ml round bottom flask was equipped with a thermocouple, condenser and a heating oil bath. The prepolymer (20 g), p-TSA (0.15 g, 0.79 mmol), 1,3,4,6-tetrakis (butoxymethyl)tetrahydroimidazo [4,5-d]imidazole-2,5(1H, 3H)-dione (11.4 g, 23.4 mmol) and 80 g of 2-hydroxyisobutyric acid methyl ester (HBM) were weighed into a flask and heated to a set temperature (50° C.) with stirring for 4 hrs. The solution was quenched with triethylamine (0.5 mL). The solution was then cooled to room temperature. The reaction mixture was precipitated with isopropyl alcohol (1000 g) and then filtered and vacuum dried for 24 hrs at 40° C.

Examples 2-4: Syntheses of Thermal Acid Generators

Example 2: Synthesis of 3-fluoropyridin-1-ium 4-methylbenzenesulfonate 4-methylbenzenesulfonic acid hydrate (75.0 g, 1.0 eq) was dissolved in tetrahydrofuran (1500 mL) and 3-fluoropyridine (40.2 g, 1.05 eq) was added dropwise while vigorously stirring at 10-20° C. for 0.5 hour. After addition, the reaction mixture was stirred at R.T. for 16 hours. It was filtered and washed by using tetrahydrofuran (750 mL). The white solid was dried under vacuum.

Example 3: Synthesis of 4-fluoropyridin-1-ium 4-methylbenzenesulfonate 4-methylbenzenesulfonic acid hydrate (25.0 g, 1.0 eq) was dissolved in tetrahydrofuran (500 mL) and 4-fluoropyridine (13.4 g, 1.05 eq) was added dropwise while vigorously stirring at 10-20° C. for 0.5 hour. After addition, the reaction mixture was stirred at R.T. for 16 hours. It was filtered and washed by using diethylether (250 mL). The white solid was dried under vacuum.

Example 4: Synthesis of 4-(trifluoromethyl)pyridin-1-ium 4-methylbenzenesulfonate 4-methylbenzenesulfonic acid hydrate (6.0 g, 1.0 eq) was dissolved in tetrahydrofuran (120 mL) and 4-(trifluoromethyl)pyridine (4.9 g 1.05 eq) was added dropwise while vigorously stirring at 10-20° C. for 0.5 hour. After addition, the reaction mixture was stirred at R.T. for 16 hours. It was filtered and washed by using diethylether (60 mL). The white solid was dried under vacuum.

Examples 5-8: Preparation of Antireflective Compositions

Example 5

0.863 g of the polymer (Example 1), 0.027 g of a tetramethoxy methyl glycoluril as a crosslinker and 0.010 g of 3-fluoropyridin-1-ium 4-methylbenzenesulfonate salt (Example 2) as a TAG were dissolved in 99.0 g of HBM solvent.

Example 6

0.863 g of the polymer (Example 1), 0.027 g of a tetramethoxy methyl glycoluril as a crosslinker and 0.010 g of 4-fluoropyridin-1-ium 4-methylbenzenesulfonate salt (Example 3) as a TAG were dissolved in 99.0 g of HBM solvent.

Example 7

0.860 g of the polymer (Example 1), 0.027 g of a tetramethoxy methyl glycoluril as a crosslinker and 0.013 g of 4-(trifluoromethyl)pyridin-1-ium 4-methylbenzenesulfonate salt (Example 4) as a TAG were dissolved in 99.0 g of HBM solvent.

Example 8: Comparative 0.866 g of the polymer (Example 1), 0.027 g of a tetramethoxy methyl glycoluril as a crosslinker and 0.007 g of ammonium 4-methylbenzenesulfonate salt as a TAG were dissolved in 99.0 g of HBM solvent.

Example 9: Evaluation of Antireflective Compositions

Antireflective compositions were evaluated for the following properties related to lithographic use 1) thickness of coated film layers, 2) on-set temperature where hardening of composition film layer first may occur, 3) composition film layer coverage, 4) optical parameters, 5) contact angle of a film layer of the composition, and 6) sublimation testing of composition film layer. The protocols as set forth in the following Table 1 were used to evaluate these properties:

TABLE 1

| Property evaluated | Instruments | Conditions |
| --- | --- | --- |
| Film thickness measurement | TEL Mark 8 track Opti-Probe Thermawave | 1500 rpm coating, baking at 205° C. for 60 sec and then thickness measurement. |
| Hardening on-set temperature test | TEL Mark 8 track & Opti-Probe Thermawave | 1500 rpm coating, baking every 10° C. temperatures from 50° C. to 200° C. for 60 sec, exposed to 30 mL PGMEA:HBM (50:50) for 90 sec on each coated film and then post baking at 110° C. for 60 sec. Thickness measurement of initial coated film with selected thermal treatment, and post baked film after stripping by organic solvent. |
| Film coverage test | TEL Mark 8 track Microscope | Wafer topology condition: Si and 1:1 trench 110 nm depth. Coating condition: Dehydration baking at 215° C. for 60 sec, HMDS treatment at 120° C. for 30 sec on bare wafer, 1500 rpm coating and then baking at 205° C. for 60 sec. Image determination by electron-microscope. |
| Optical parameters | J. A. Woollam VUV-Vase | n/k @ 193 nm measured by ellipsometer around 600~800 Å film layer thickness. |
| Contact Angle | JDSA-100 Goniometer | 9 points water contact angle measurement by 3 ul of DIW loading with static method. |
| Sublimation test | QCM | QCM measurement for baking at 205° C. for 60 sec a coated wafer. |

Results

Part 1: Optical and Functional Test Performance.

Film layers of antireflective compositions of each of Examples 5, 6, 7, and 8 were spin-coated onto silicon wafers and evaluated for optical parameters with 193 nm radiation, contact angle and relative sublimation as described in Table 1 above. Results are set forth in the following Table 2.

TABLE 2 n/k value @ 193 nm, contact angle and sublimation results

| Formulation | Optical parameters @ 193 nm wavelength | | Contact angle (°) | Relative sublimation (Å) |
| --- | --- | --- | --- | --- |
| | n value | k value | | |
| Example 5 | 1.95 | 0.27 | 55 | 1.1 |
| Example 6 | 1.95 | 0.27 | 55 | 1.0 |
| Example 7 | 1.95 | 0.26 | 56 | 1.2 |
| Example 8 (Comparative). | 1.95 | 0.26 | 55 | 1.0 |

Part 2: On-Set Temperature and Film Coverage Results.

Film layers of antireflective compositions of each of Examples 5, 6, 7, and 8 were spin-coated onto silicon wafers and evaluated for on-set temperature and film coverage as described in Table 1 above. Results are set forth in the following Table 3. As discussed in Table 3, the antireflective compositions of the Examples 5, 6 and 7 exhibited lower on-set temperature (90° C.→60° C.). The antireflective compositions of the Examples 5, 6 and 7 also provided much improved film coverage property than Example 8 (Comparative).

TABLE 3

Film coverage results by on-set temperature.

| Formulation | On-set temperature (° C.) | Film coverage property |
| --- | --- | --- |
| Example 5 | 60 | Excellent |
| Example 6 | 60 | Excellent |
| Example 7 | 60 | Excellent |
| Example 8 (Comparative). | 90 | Lower quality relative to Example 5-7 |

What is claimed is:

1. A method for forming a photoresist relief image, comprising:
   a) applying on a substrate a layer of a coating composition comprising: 1) a resin; and 2) a solvent component; and 3) a thermal acid generator comprising a structure of Formula (I):

X⊖⊕YH  (I)

wherein Y has a structure of Formula (II):

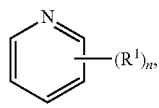  (II)

each $R^1$ is independently $C_1$-$C_6$ haloalkyl, —CN, —$NO_2$, —$COR^2$, —$COOR^2$, —$CONR^2$ or —$SO_2R^2$;
   $R^2$ is independently hydrogen, $C_1$-$C_6$ alkyl, $C_3$-$C_6$ cycloalkyl or phenyl, which may be optionally substituted;
   n is an integer from 1 to 5; and
   X is an anion component; and
   b) applying a layer of a photoresist composition above the coating composition layer; and
   c) exposing the photoresist layer to patterned activating radiation and developing the exposed photoresist layer to form a photoresist life image.

2. A method of any one of claim 1 wherein the coating composition comprises a hydrophilic resin.

3. The method of claim 1 wherein each $R^1$ is independently —$COR^2$, —$COOR^2$, —$CONR^2$ or —$SO_2R^2$.

4. The method of claim 1 wherein each $R^1$ is independently $CF_3$, —CN, —$NO_2$, acetyl or ester.

5. The method of claim 1 wherein $R^1$ is ester that is not reactive during lithographic processing.

6. The method of claim 1 wherein the thermal acid generator compound has a structure of the following Formula (A), (B) or (C):

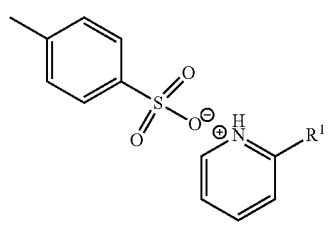 (A)

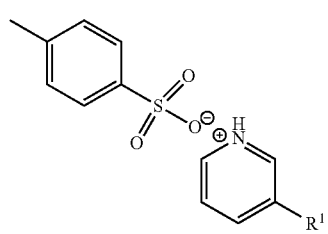 (B)

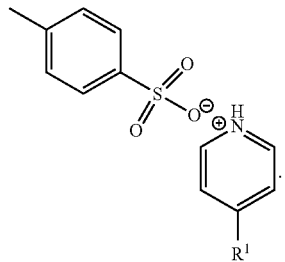 (C)

7. The method of claim 1 wherein YH of Formula (II) is one of the following structures:

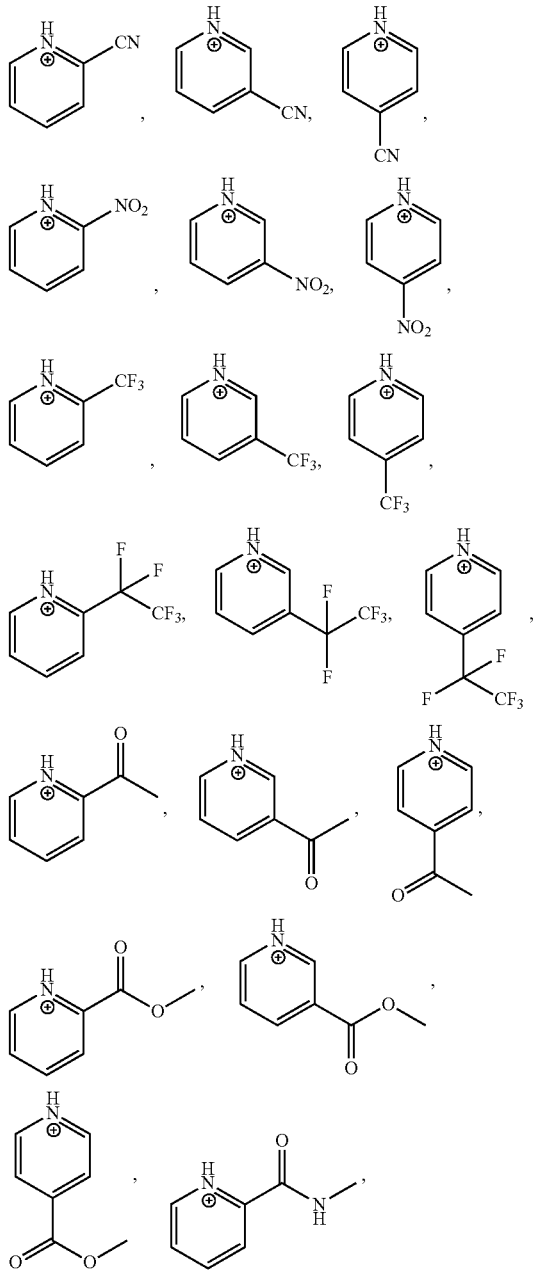

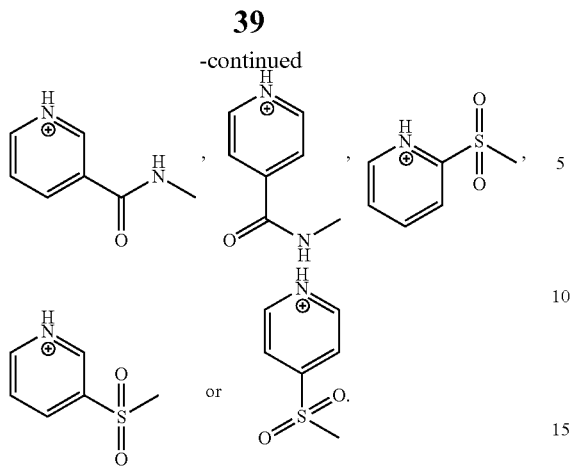

8. A coated substrate comprising:
a substrate comprising
a) a coating composition comprising: 1) a resin; and 2) a thermal acid generator comprising a structure of Formula (I):

$$X^{\ominus} {}^{\oplus}YH \qquad (I)$$

wherein Y has a structure of Formula (II):

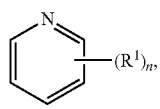

(II)

each $R^1$ is independently halogen, $C_1$-$C_6$ haloalkyl, —CN, —$NO_2$, —$COR^2$, —$COOR^2$, —$CONR^2$ or —$SO_2R^2$;
$R^2$ is independently hydrogen, $C_1$-$C_6$ alkyl, $C_3$-$C_6$ cycloalkyl or phenyl, which may be optionally substituted;
n is an integer from 1 to 5; and
X is an anion component; and
b) a layer of a photoresist composition above the coating composition layer.

9. The substrate of claim 8 wherein YH of Formula (I) is one of the following structures:

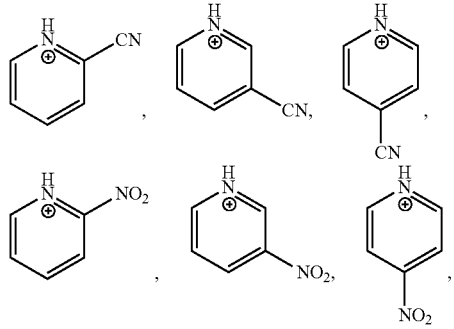

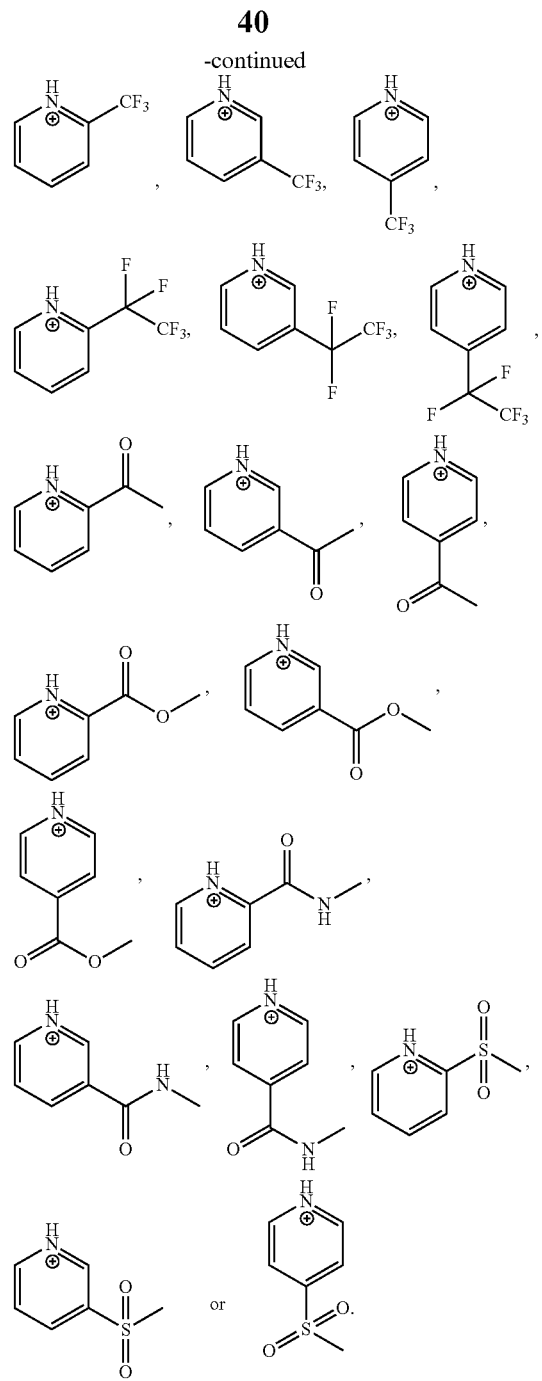

10. The substrate of claim 8 wherein each $R^1$ is independently —$COR^2$, —$COOR^2$, —$CONR^2$ or —$SO_2R^2$.

11. The substrate of claim 8 wherein each R' is independently $CF_3$, —CN, —$NO_2$, acetyl or ester.

12. The substrate of claim 8 wherein $R^1$ is ester that is not reactive during lithographic processing.

* * * * *